(12) United States Patent
Bickmore, Jr. et al.

(10) Patent No.: US 7,504,219 B2
(45) Date of Patent: Mar. 17, 2009

(54) METHODS AND APPARATUS FOR AMPLIFICATION OF DNA USING SONIC ENERGY

(75) Inventors: William D. Bickmore, Jr., St. George, UT (US); Danvern Ray Roberts, Las Vegas, NV (US)

(73) Assignee: DxNA LLC, St. George, UT (US)

( * ) Notice: Subject to any disclaimer, the term of this patent is extended or adjusted under 35 U.S.C. 154(b) by 0 days.

(21) Appl. No.: 11/432,935

(22) Filed: May 12, 2006

(65) Prior Publication Data

US 2006/0270022 A1 Nov. 30, 2006

Related U.S. Application Data (60) Provisional application No. 60/680,738, filed on May 13, 2005.

(51) Int. Cl.
*C12Q 1/68* (2006.01)
*C12P 19/34* (2006.01)

(52) U.S. Cl. ......................................... 435/6; 435/91.2

(58) Field of Classification Search ...................... None
See application file for complete search history.

(56) References Cited

U.S. PATENT DOCUMENTS

| 2006/0152727 | A1 | 7/2006 | Bickmore, Jr. et al. |
| 2006/0188891 | A1 | 8/2006 | Bickmore, Jr. et al. |

FOREIGN PATENT DOCUMENTS

| WO | WO 98/06876 | * | 2/1998 |

* cited by examiner

*Primary Examiner*—Kenneth R. Horlick
*Assistant Examiner*—David C Thomas
(74) *Attorney, Agent, or Firm*—Holme Roberts & Owen LLP (57) ABSTRACT

Apparatus and methods for amplification of DNA are provided that use sonic energy in place of conventional thermocyclers. In one embodiment, sonic energy is applied to a PCR cocktail to effect dissociation of double stranded DNA into single strands of DNA. A quiescence stage, where no sonic energy is applied, results in amplification of DNA. Repetition of the cycles of application of sonic energy and cessation of application of sonic energy results in DNA amplification.

18 Claims, 8 Drawing Sheets

METHODS AND APPARATUS FOR AMPLIFICATION OF DNA USING SONIC ENERGY

CROSS-REFERENCE TO RELATED APPLICATIONS

This application claims priority to Provisional Application No. 60/680,738, entitled "Methods and Apparatus for Amplification of DNA Using Sonic Energy," and filed on May 13, 2005, and incorporates said provisional application herein in its entirety.

BACKGROUND OF THE INVENTION

1. The Field of the Invention

The present invention is directed to a methods and apparatus for amplification of DNA.

2. The Relevant Technology

Molecular biology and associated applications rely heavily on the ability to manufacture large amounts of genetic material from small samples so that one can engage in activities such as the identification of particular genetic material in a sample, the measurement of how much genetic material was present, and generation of enough genetic material for use to serve as a component of further applications.

The most successful tool for this purpose is generally known as the "polymerase chain reaction" (PCR). The PCR process is generally performed in a small reaction vial containing constituents for DNA duplication: the DNA to be duplicated, the four nucleotides which are assembled to form DNA, two different types of synthetic DNA called "primers" (one for each of the complementary strands of DNA), salts, and an enzyme called DNA polymerase. These constituents are often referred to as the PCR "cocktail."

DNA is double stranded. The PCR process begins by separating the two strands of DNA into individual complementary strands, a step which is generally referred to as "denaturation." This is typically accomplished by heating the PCR reaction mixture to a temperature of about 94 to about 96 degrees centigrade for a period of time between a few seconds to over a minute in duration.

Once the DNA is separated into single strands, the mixture is cooled to about 45 to about 60 degrees centigrade (typically chosen to be about 5 degrees below the temperature at which the primer will melt) in order to allow a primer to bind to each of the corresponding single strands of DNA in the mixture (this involves providing both "upstream" and "downstream" primers). This step is typically called "annealing." The annealing step typically takes anywhere from a few seconds up to a few minutes.

Next, the reaction vessel is heated to about 72 to 73 degrees centigrade, a temperature at which DNA polymerase in the reaction mixture acts to build a second strand of DNA onto the single strand by adding nucleic acids onto the primer so as to form a double stranded DNA that is identical to that of the original strand of DNA. This step is generally called "extension." The extension step generally takes from a few seconds to a couple minutes to complete.

This series of three steps, also sometimes referred to as "stages," define one "cycle." Hypothetically, proper completion of a PCR cycle results in doubling the amount of DNA in the reaction vial. Repeating a cycle results in another doubling of the amount of DNA in the reaction vial. Typically, the process is repeated many times, e.g. 10 to 40 times, resulting in a large number of identical pieces of DNA. Performing 20 cycles results in more than a million copies of the original DNA sample. Performing 30 cycles results in more than a billion copies of the original DNA sample.

A "thermocycler" is used to automate the process of moving the reaction vessel between the desired temperatures for the desired period of time. Conventional thermocyclers typically require about three hours to run 30 cycles, due to the amount of time required to accomplish a change in temperature for each PCR step, as well as the time required at each target temperature. It would be of great interest in many situations if one could obtain the benefits of PCR more quickly than this.

More recently, thermocyclers have been made available that omit a separate extension stage, and operate as a two stage thermocycler. The first stage of this two stage system is denaturation, and the second stage is annealing, with extension occurring simultaneously with annealing. Although this approach tends to save some time over a three-stage thermocycler, it would still be advantageous to reduce the time required by conventional thermocyclers.

BRIEF SUMMARY OF THE INVENTION

The present invention provides methods and apparatus for amplification of DNA.

The present invention involves the use of pulses of sonic energy in place of conventional thermocyclers. In one embodiment, sonic energy is applied to a PCR cocktail to effect dissociation of double stranded DNA into single strands of DNA. A quiescence stage, where no sonic energy is applied, results in amplification of DNA. This two step sonic PCR cycle may be repeated as many times as desired; repetition of the cycles of the application of sonic energy and cessation of the application of sonic energy results in DNA amplification.

These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The present invention provides methods and apparatus for DNA amplification.

As discussed above, the polymerase chain reaction (PCR) is a very effective method for amplifying DNA. The present invention takes advantage of the simplicity of the science of PCR and upon the surprising discovery that application of sonic energy is effective to separate double stranded DNA into single strands without damaging the polymerase enzyme or any other constituents of a PCR cocktail, and that the single strands of DNA thus formed will then serve as templates for building of double stranded DNA when the application of sonic energy is discontinued.

As used herein, the term "sonic" shall be used to refer not only to sound in the frequency range audible to human ears, but also to sounds above and below such frequencies, which are sometimes referred to in other contexts as ultrasonic and subsonic frequencies, respectively.

The use of sonic energy to effect PCR has been found to result in a number of advantages. For example, it has been discovered that sonic energy is effective in separating double stranded DNA into single strands over a wide range of temperatures extending from near freezing to just below the temperature at which the polymerase becomes inoperative. Not only does this greatly simplify the design and operation of the amplification apparatus, but it allows the use of polymerase enzymes that are not thermostable, in contrast to the requirements for polymerase enzymes used in conventional thermocycle PCR systems. Successful sonic PCR has been demonstrated using a mesophilic DNA polymerase (Klenow Fragment (3'->5' exo$^-$)) at room temperatures (roughly 20 to 37 degrees C.).

The sonic PCR process may take different forms, but will be described in the following paragraphs as a two step process. A container holding a reaction mixture cocktail including DNA to be amplified, a polymerase enzyme, nucleosides, salts and the appropriate primers is subjected to sonic energy for a time sufficient to separate the double stranded DNA into single strands. This step shall be referred to herein as "dissociation" to distinguish it from "denaturation" effected by thermal treatment of conventional systems, although the dissociation step is analogous to denaturation. Although the inventors do not wish to be bound by theory, it is theorized that the application of sonic energy breaks the hydrogen bonding between the complementary strands of double stranded DNA.

It will be appreciated that the amount of time required to effect dissociation may vary depending upon additional factors, such as the frequency of the sonic energy and the power of the sonic energy. It has been observed empirically that application of only a few milliwatts of power to a transducer at some frequencies rapidly dissociates double stranded DNA in a PCR cocktail in just a couple of seconds.

Following the application of sonic energy sufficient to effect dissociation, the second step of the two step sonic PCR process simply involves discontinuance of the application of sonic energy for a time sufficient to allow the primers to attach to the single strands of DNA and for the polymerase enzyme to build a complementary strand of DNA onto each single strand of DNA in the reaction cocktail. This step shall be sometimes be referred to interchangeably herein as "discontinuance" or "discontinuing" of sonic energy, and is sometimes referred to herein as the "quiescence" stage. The amount of time actually required in the quiescence stage may vary from cycle to cycle, and may vary depending upon factors such as the particular DNA involved, the polymerase enzyme being used, the temperature of the cocktail, and other factors.

It has been observed empirically that a duration of from about 0.5 to about 3 seconds is typically adequate to allow complete amplification of the singled stranded DNA in the cocktail following the application of sonic energy in the dissociation step.

The dissociation and quiescence steps (also sometimes referred to as "stages") define one sonic PCR cycle. If complete dissociation occurs of the double stranded DNA in the cocktail, followed by complete formation of complementary strands onto each single stranded DNA, each cycle will result in doubling of the amount of DNA in the cocktail. Additional cycles may be repeated until a desired amount of DNA is obtained.

Although a simple control system may be used to run multiple cycles of a sonic PCR system, just as simple control systems are often used with thermocyclers, it is preferred that a computer, programmable logic controller, or microprocessor be used to control each cycle in view of empirical observations that the amount of time required to complete the desired formation of single stranded DNA, then formation of double stranded DNA, will change from cycle to cycle. Hence, it has been discovered that optimum control of a PCR process involves real-time monitoring and controlling of each stage of a sonic PCR amplification procedure in order to insure the desired reactions of each stage are allowed to finish before moving on to the next stage. Copending applications have been filed by the assignee of the present application which describe suitable approaches for monitoring the PCR process and for controlling each step so as to optimize the process. U.S. patent application Ser. No. 11/031,526, entitled "Fluorescence Detection System", was filed Jan. 7, 2005. U.S. patent application Ser. No. 11/063,352, entitled "Methods and Apparatus for Controlling DNA Amplification" was filed Feb. 23, 2005. Both of these copending applications are incorporated herein in their entirety by reference. The subject matter of either or both of these applications is useful to enhance a sonic PCR system, although significant advantages arise even in the absence of these enhancements. It is contemplated that other approaches may be used as alternatives to those set forth in these copending applications.

Figure 1:
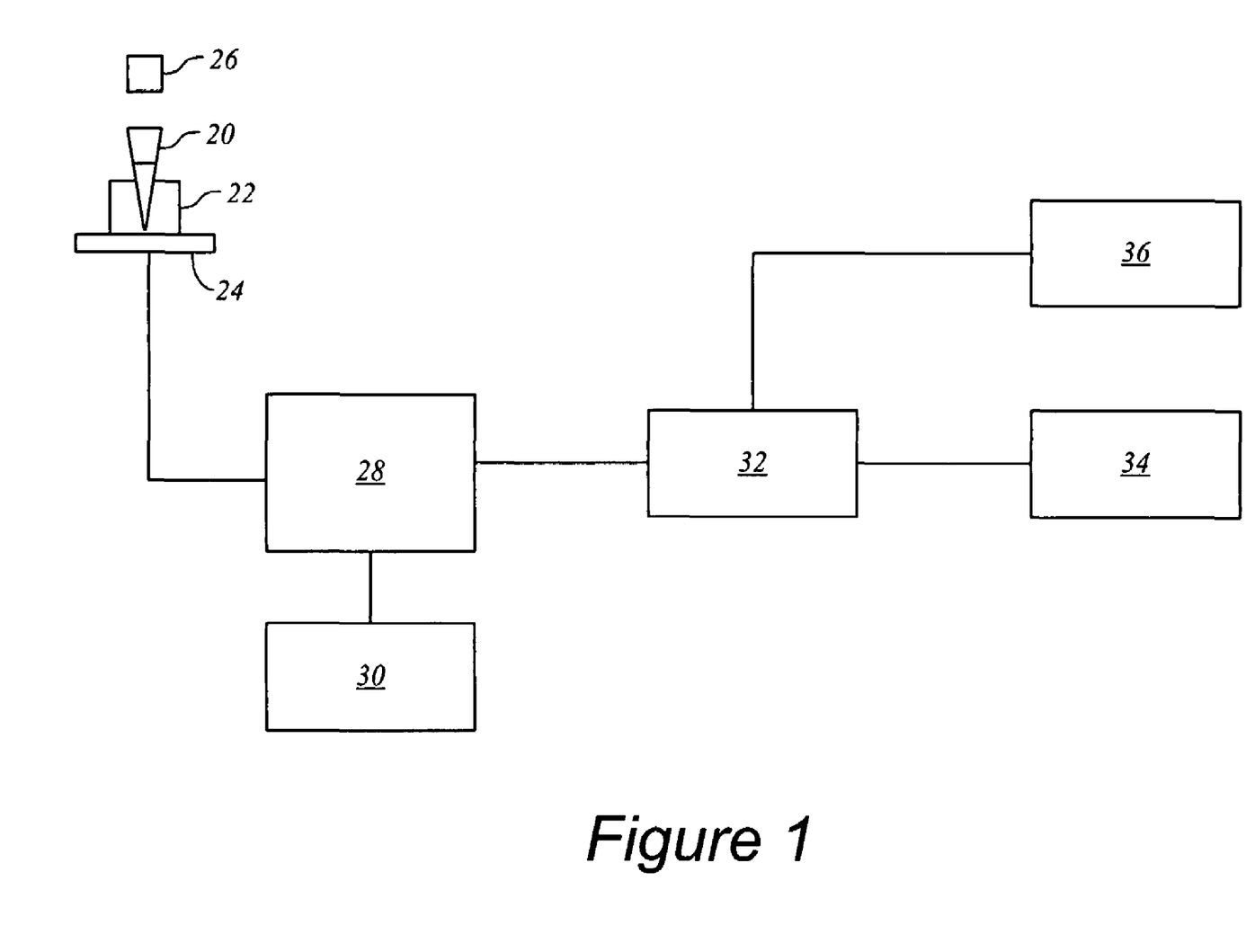
FIG. 1 is a schematic representation of one embodiment of the apparatus of the invention.

An embodiment of the present invention is depicted in schematic form in FIG. 1, which illustrates the use of a sample vial 20 to contain the PCR cocktail. It will be appreciated that it is not required to use vials; one of ordinary skill will appreciate from the teachings herein that one could provide a multi-well plate or other structure in place of individual vials.

FIG. 1 illustrates use of a vial holder 22. A sonic transducer 24 or other source of sonic energy is placed so as to allow sonic energy to enter vial 20. A fluorescence system 26 is advantageously provided to excite fluorescent material present in the sample cocktail and to detect fluorescent emissions. It will be appreciated that when it is desired to monitor the progress of PCR, alternative systems may be used in place of a fluorescence system, such as a spectrophotometer. Alternatively, monitoring of the progress of PCR may be omitted, as is the case in typical thermocyclers.

Figure 2:
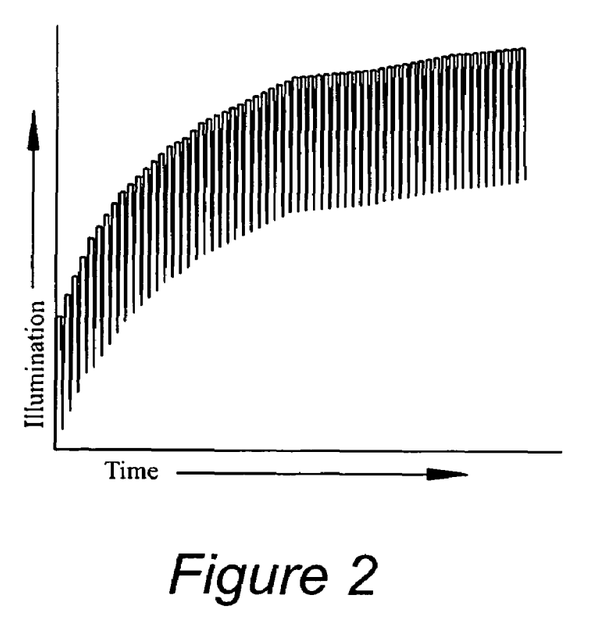
FIG. 2 is a graph showing changes in fluorescent illumination over time in a situation involving DNA amplification using sonic PCR.

FIG. 2 illustrates a typical curve showing changes in fluorescent illumination over time where amplification is occurring in a system in which the fluorescent source emits most brightly in the presence of double stranded DNA and less brightly in the presence of single stranded DNA.

Figure 3:
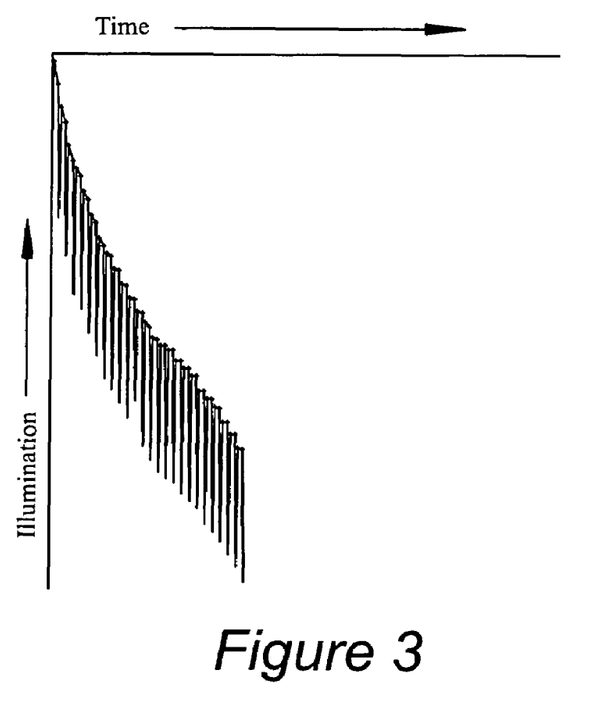
FIG. 3 is a graph showing changes in fluorescent illumination over time in a situation where no DNA amplification was occurring.

FIG. 3 shows the decrease in peak and valley readings of fluorescent illumination over time in a circumstance where amplification was not occurring. The ever diminishing luminescence over time is characteristic of fluorescence tagged indicators, which is believed to occur due to fluorescent decay caused by continuous exposure of bright stimulating light.

Returning to FIG. 1, a pulse duration controller 28 may be provided to control the application of sonic energy applied to the sample in vial 20. Frequency generator 30 is used to control pulse duration controller 28. Frequency generator 30 may be a separate device, as shown in FIG. 1, or may be part of computer 32, which performs control functions for the sonic PCR cycler. Display 34 is useful for outputting visual information to a user, and for use in making user changes to various settings. A printer 36 may also be useful for printing out records relating to an amplification. Alternatively, printer 36 may be omitted altogether, or replaced by a data processing computer or some other output device or devices.

Figure 4:
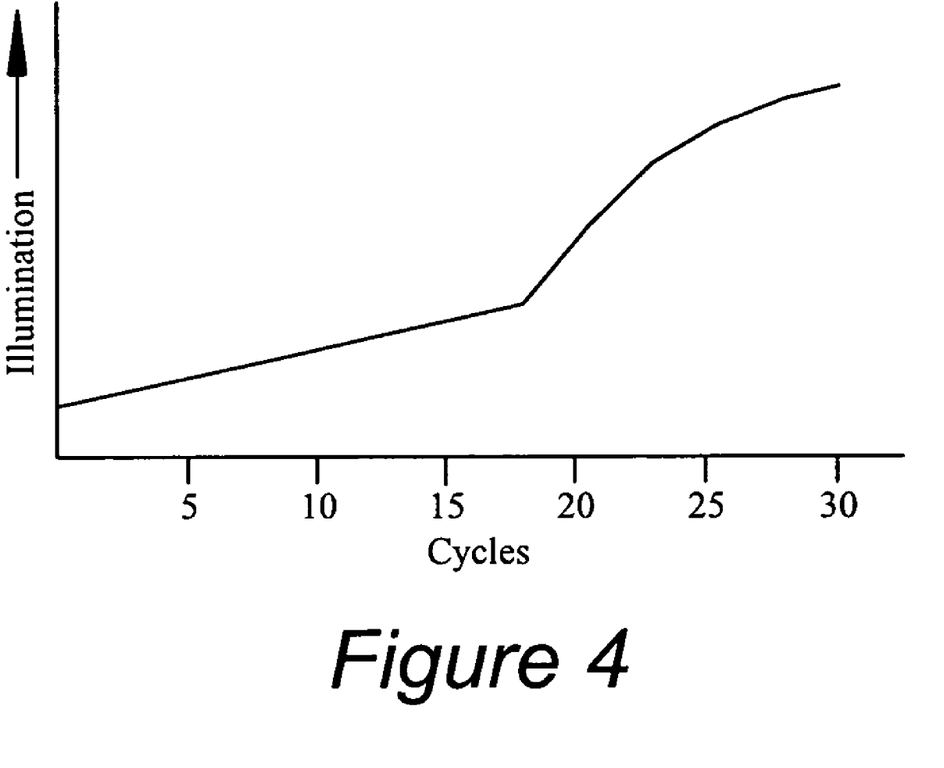
FIG. 4 is graph showing illumination over time in a conventional thermocycler system.

Sonic PCR is much faster than conventional thermocycle PCR. It has been discovered by the assignee of the present application that traditional thermocycle PCR does not provide a true doubling of DNA each cycle during the first 15 to 20 cycles, as illustrated in FIG. 4, which depicts the results observed spectrophotometrically in connection with one thermocycle-based PCR experiment. Empirical spectrophotometer observations of sonic PCR suggest that a true doubling occurs from the first sonic cycle, and the relative absence of non-completed DNA fragments.

Electrophoresis band analysis of the final products of traditional thermocycler PCR and sonic PCR verify that with the proper selection of enzymes and primers the DNA products of the two processes are comparable.

Sonic PCR utilizes much less energy than thermocycler PCR. A conventional thermocycler utilizes a significant amount of energy to change the temperature of the sample cocktail between the thermocycle temperatures. Indeed, some conventional thermocyclers require from 1 to 10 kilowatts of continuous power. The lack of any need for heat exchanger components, and the small size of a sonic transducer also allows a sonic PCR system to be quite small and to use very little power. The small amount of power required to operate a sonic PCR device makes it conceivable to operate it on battery power, and existing off the shelf components allow a sonic PCR device to measure only about 4 inches by 6 inches by 2 inches. Sonic PCR can be used in the field to identify harmful pathogens in less than 10 minutes from sample preparation to final diagnostic results. Empirical testing shows sonic PCR to have equivalent accuracy to laboratory-based thermal PCR.

Figure 5:
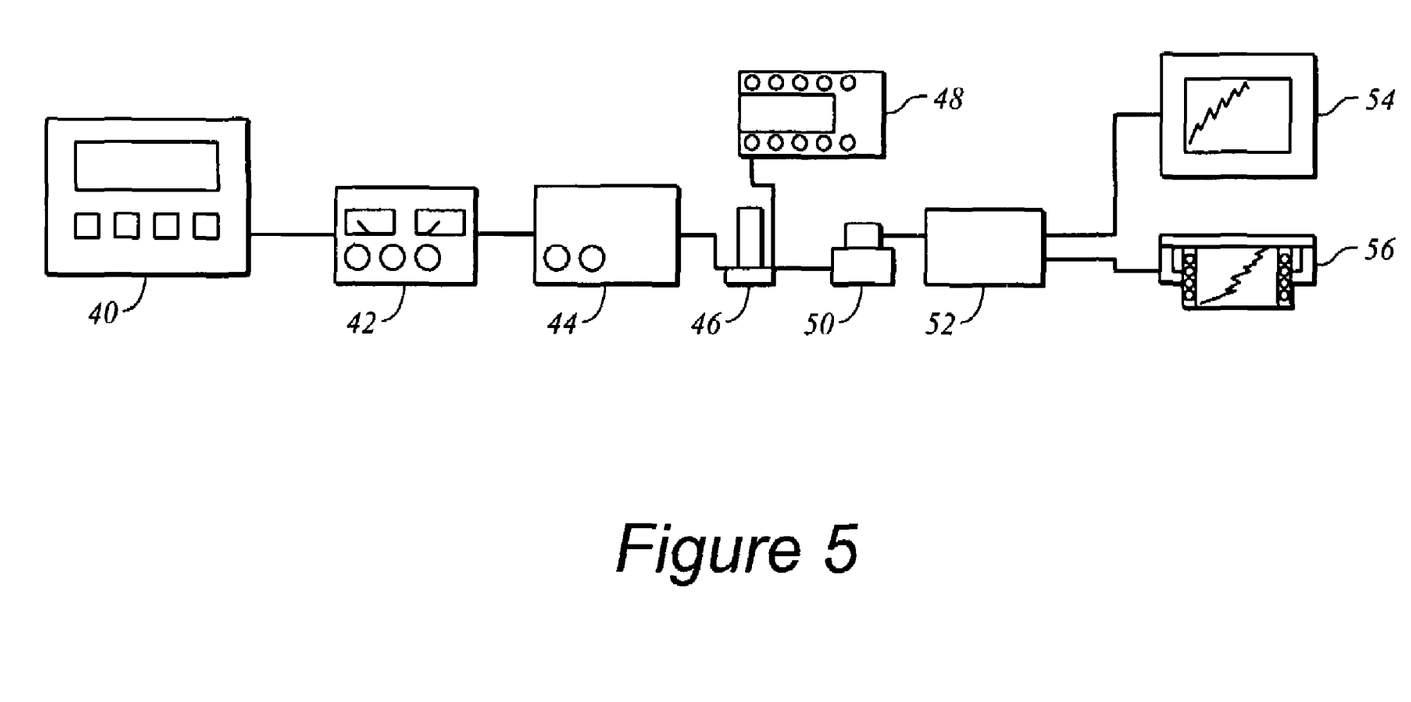
FIG. 5 depicts schematically a set up for performing sonic PCR.

Sonic PCR has been found effective over a wide range of sonic frequencies. FIG. 5 depicts schematically one embodiment of an apparatus useful for effecting sonic PCR. Frequency generator 40 was used to generate a particular sonic frequency for testing. An amplifier 42 was found useful in connection with some tests, possibly due to limitations in the particular transducer being used to generate sonic energy. A matching standing wave ratio (SWR) bridge 44 was also found useful under some circumstances, again possibly due to limitations in the particular transducer being used. Power relay 46 was advantageously controlled by pulse timer 48. A transducer assembly 50 was used to apply desired frequencies of sonic energy to the cocktail. The transducer assembly also advantageously included a fluorescence system for monitoring the status of DNA amplification over time. The output of the fluorescence system was fed into signal amplifier 52, and the test apparatus advantageously included both a video display 54 and a strip chart recorder 56.

The cocktail for each of these tests included human β-globin DNA, an upstream and a downstream primer associated with a template of interest on the DNA, and the customary salts, nucleotides, and polymerase. The cocktail also included a fluorescein labeled Taqman® probe for use in monitoring DNA amplification via proportional increase in fluorescence levels with the increase in DNA. A portion of the cocktail was tested for successful amplification using a conventional thermocycler. The sonic PCR system was operated at room temperature. In order for the Taqman® probe to operate efficiently at room temperature a proper polymerase enzyme must be selected.

Two different transducers were tested. One was a piezoelectric transducer constructed around a common piezoelectric annunciation device as is commonly used to produce an audible warning tone for electronics. An electromagnetic transducer was used to produce some sounds. It was necessary to add substantial amplification in the form of a variable gain 100 watt power supply when operating in the range of 3500 Hz to 500 KHz. Above 500 KHz. It was also necessary to add a standing wave ratio (SWR) bridge to the equipment to compensate for a significant impedance mismatch between the amplifier and the particular piezoelectric transducer being used. It is believed that that use of a more suitable transducer for a given frequency would simplify the set up.

Figure 6:
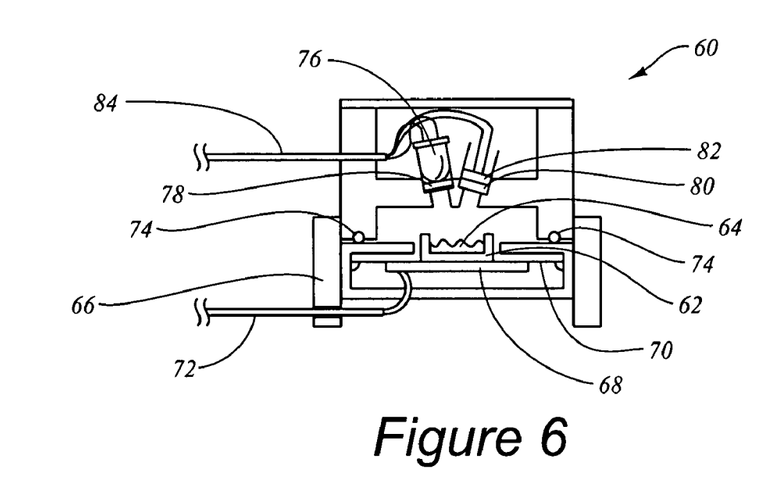
FIG. 6 depicts a piezoelectric transducer system.

FIG. 6 depicts piezoelectric transducer assembly 60. A sample cup 60 was used to hold the DNA amplification cocktail 64. A chassis 66 was used to hold a piezocrystal 68 in contact with a metallic membrane 70 associated with sample cup 62. Wire 72 led to the crystal driver. A removable fluorescence optics assembly of the type disclosed in copending application Ser. No. 11/031,526, entitled "Fluorescence Detection System", filed Jan. 7, 2005 and incorporated above by reference, included LED 76 to emit light in the excitation range of the fluorescence tag, excitation filter 78, emission filter 80, and a cadmium sulfide photo receiver 82. A wire 84 was connected to the optics assembly electronics. Light seal 96 was used to prevent unwanted light from striking the cocktail or photo receiver 82.

Figure 7:
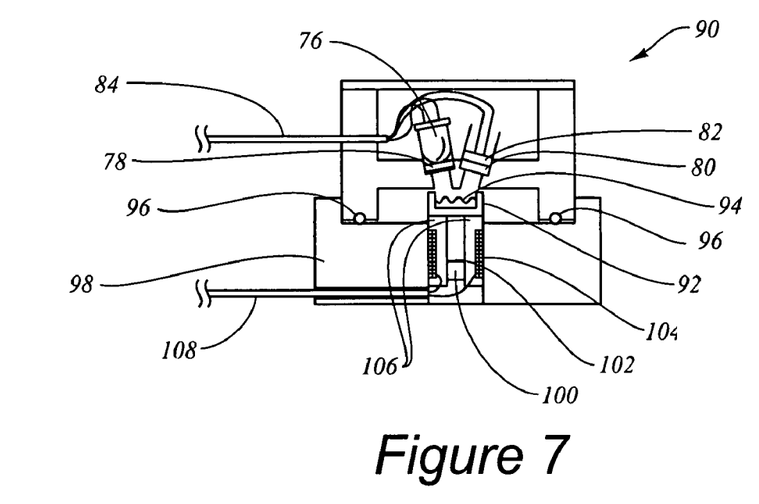
FIG. 7 depicts an electromagnetic transducer system.

FIG. 7 depicts the slightly different arrangement used in connection with electromagnetic transducer assembly 90. A similar sample cup 92 having a receptacle for the cocktail 94 was used, and a light seal 96 was also provided to receive the same fluorescence optical assembly described above. Chassis 98 served as a base for magnet 100, armature 102, and coil 104. Elastomer 106 was also used. A wire 108 leads to the coil driver.

In each experiment, power relay 46 was used to gate the pulse of electrical energy to the transducer. The on and off timing of relay 46 was controlled by a programmable logic controller. The electronic signal from the cadmium sulfide photo receiver was amplified and the result simultaneously displayed on a video display with a time memory function and a chart recorder. In each test, a 5 µL aliquot of the cocktail was placed in the sample cup. The background fluorescence was noted. The frequency of frequency generator 40 was adjusted as desired and the amount of fluorescence was observed over time. The fluorescent probe used in these tests glows less brightly when single stranded DNA is present, and more brightly when double stranded DNA is present.

Once the operating frequency was established, dissociation pulses of 2 seconds were delivered, followed by quiescence for 11 seconds. Hence, a full sonic PCR cycle, in this example was 13 seconds. This 13 second cycle was found to induce DNA amplification similar to a 2-3 minute cycle using a conventional thermocycler. Sonic PCR was observed to be much more robust, especially in the initial cycles, than a conventional thermocycler.

The results of tests at various sonic frequencies is reported in Table 1.

TABLE

Selected Operation Points

| Frequency in Hertz | Power in Watts | Transducer Type |
| --- | --- | --- |
| 2 | >.001 | Piezoelectric |
| 60 | >.001 | Piezoelectric |
| 90 | >.001 | Piezoelectric |
| 130 | >.001 | Piezoelectric |
| 170 | >.001 | Piezoelectric |
| 240 | 20 | Electromagnetic |
| 320 | 1.5 | Electromagnetic |
| 2.7K | 0.002 | Piezoelectric |
| 14K | 0.5 | Piezoelectric |
| 300K | 8 | Piezoelectric |
| 4M | 40 | Piezoelectric |
| 14M | 100 | Piezoelectric |
| 21M | 100 | Piezoelectric |
| 44M | 100 | Piezoelectric |

Use of sonic energy for DNA amplification was tested over a large area of the sonic spectrum, from 2 Hertz to 44 MHz, and was effective at every frequency tested.

Only 0.002 watts were required at 2.7 KHz. This level of power consumption is more than one million times less than that used by a conventional thermocycler operating at 2-10 KW. When allowances are made for a typical sonic duty cycle of less than 20%, the energy consumption is some five million times less. Even at the worst case of a mismatch of impedance at 14 MHz, the low power consumption is remarkable. Should one desire to operate at high ultrasonic frequencies, then obtaining transducers which have resonance near the desired frequency would seem likely to result in significant increases of efficiency.

It has been discovered that it is not necessary to establish a standing wave in order to effect sonic PCR power levels required are amazingly low, in contrast to thermocyclers.

It was found that increasing power too much could result in damage to the DNA rather than just dissociation.

It is possible to apply sonic energy in various wave patterns, although it appears that square waves are the most efficient.

From the empirical testing it is apparent that sonic PCR is possible over a wide range of frequencies. Since many frequencies are within the auditory range of humans, it is currently preferred to use an operating sonic frequency at about 20 KHz, which is at about the upper hearing limit of most people and hence provides for quieter operation. Of course, as new transducers are tested or become available, the favored sonic frequency may change.

Figure 8:
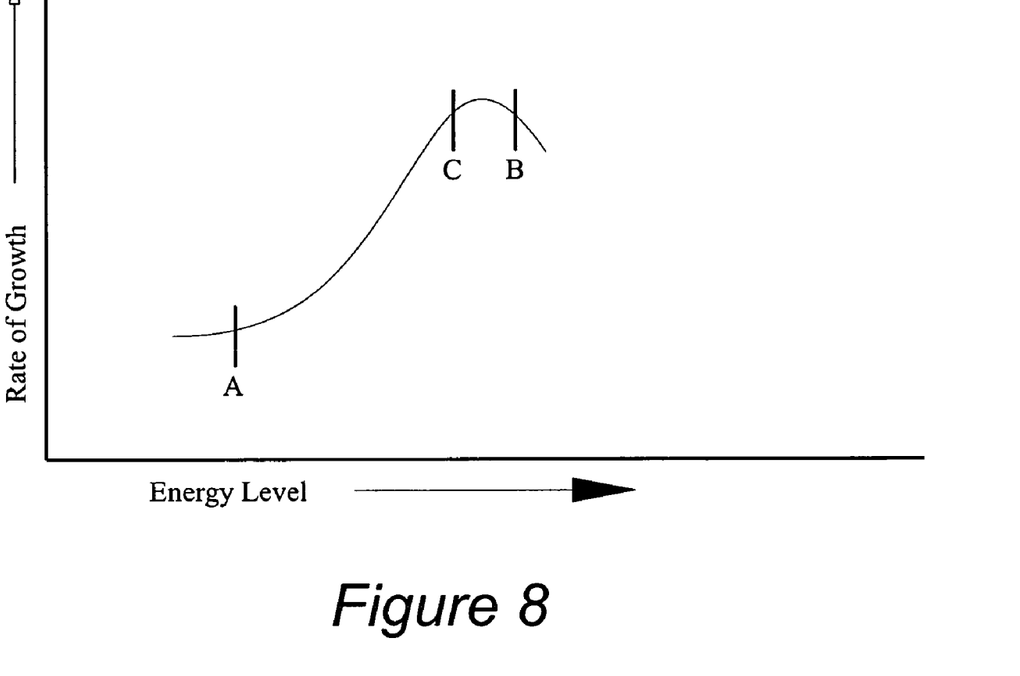
FIG. 8 is a graph showing the effects of increasing energy on the rate of growth.

Various methods may be used to optimize energy levels and other parameters of sonic PCR. FIG. 8 depicts a graph showing the effects of increasing energy on the rate of growth. This graph may be generated by providing a suitable detection system for determining whether DNA is in a double stranded or single stranded configuration. Once a sonic frequency has been selected, a low energy level, e.g., Point "A," is selected that is likely to effect dissociation. Several sonic PCR cycles may then be performed while the rate of growth is observed. This growth rate is recorded. The energy level is then increased, and additional sonic PCR cycles observed so that a comparison may be made between the rate of growth at the new energy level with that of the prior energy level(s). This process is continued until the rate of growth begins to decline (Point "B"). The energy level is then incrementally decreased until the rate of growth declines (Point "C"). An optimum operating energy level is between Points B and C. This process can be used for periodic calibrations of a particular sonic PCR apparatus, or may be used for each PCR procedure on an ongoing basis, perhaps by starting at an energy level of Point C rather than at Point A so as to streamline the process.

Figure 9:
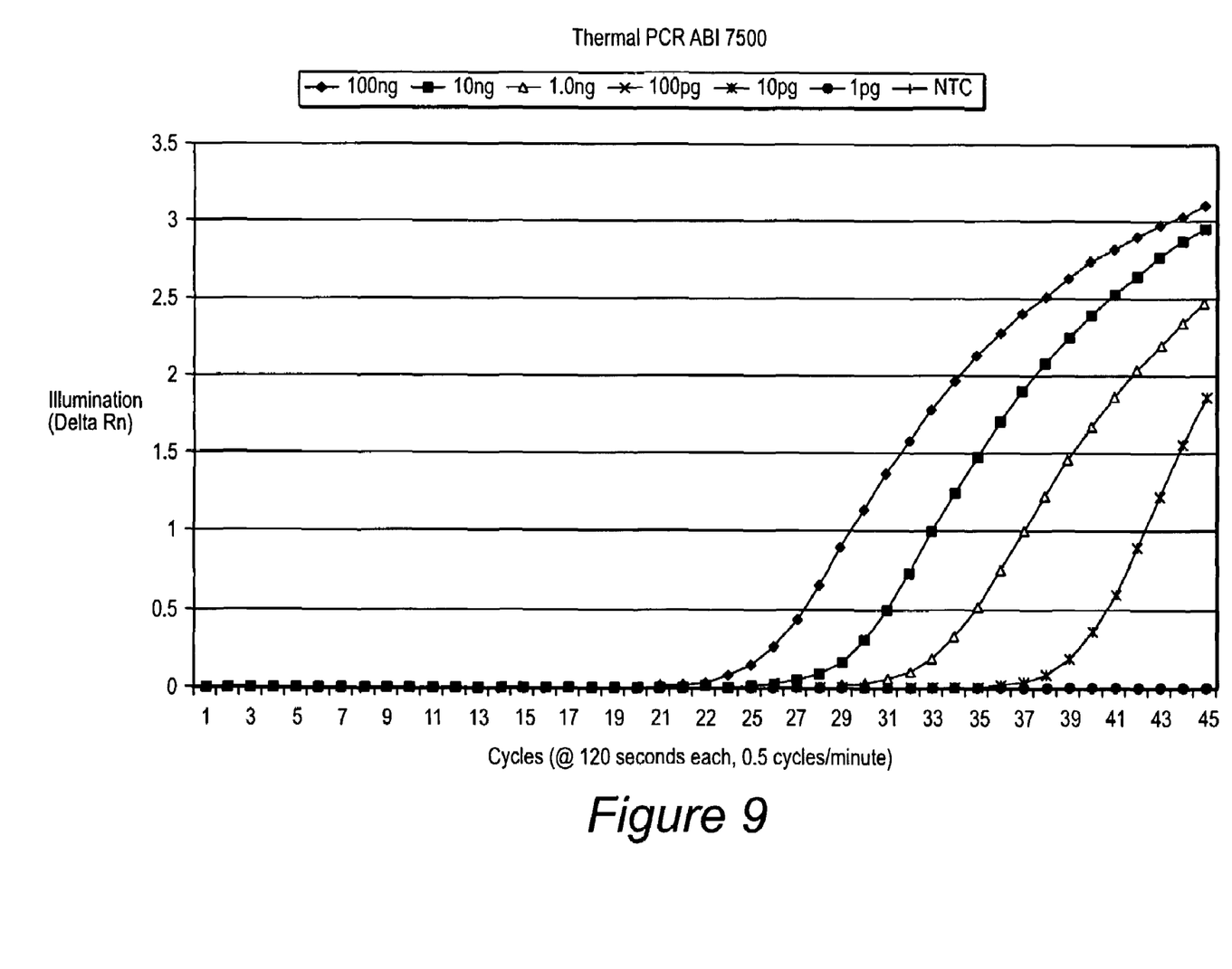
FIG. 9 is a graph showing a sensitivity study of a commercial thermal PCR system.
Figure 10:
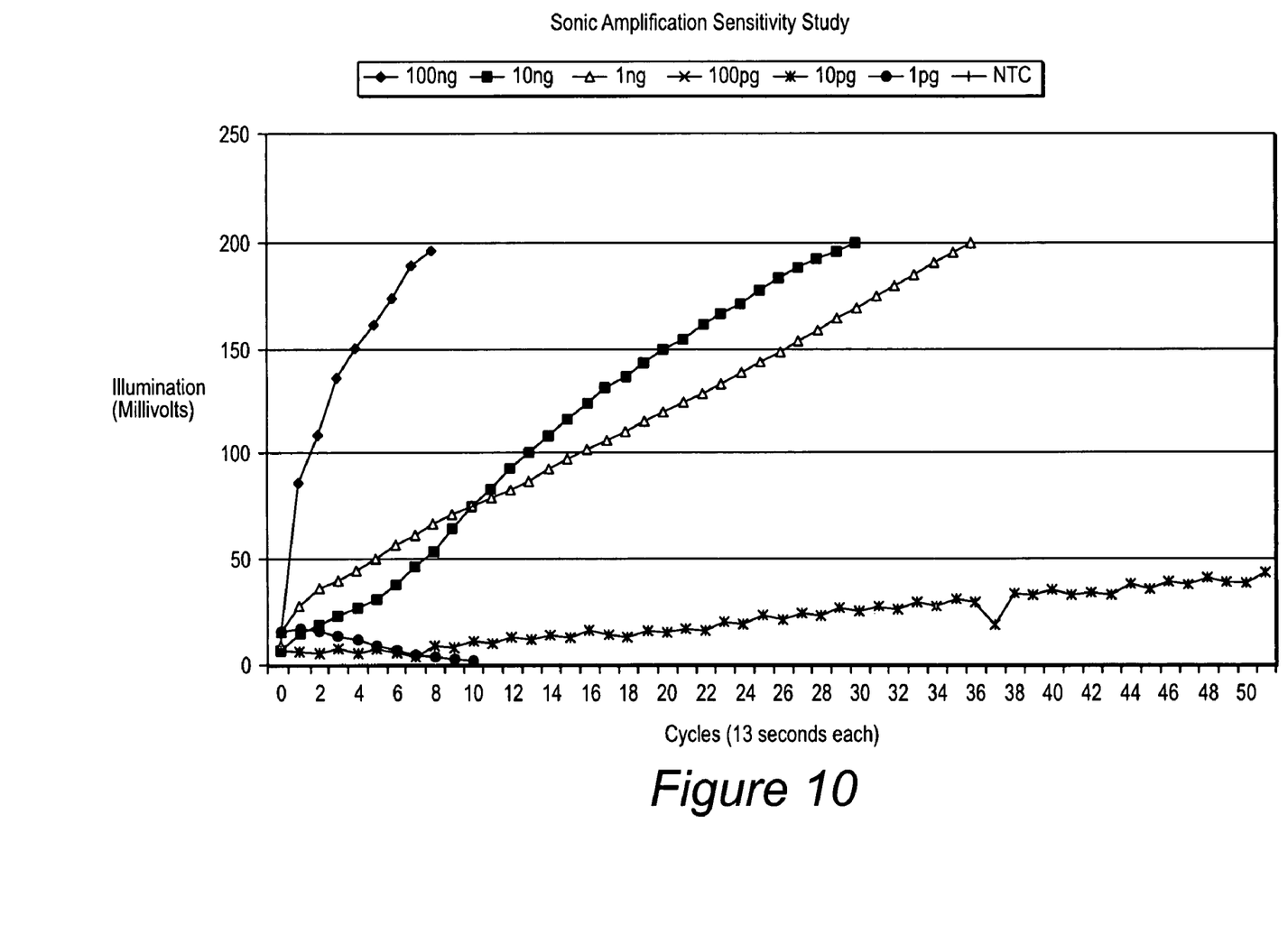
FIG. 10 is a graph showing a sensitivity study of a sonic PCR experiment.

FIGS. 9 and 10 show the results of sensitivity experiments performed using a conventional thermal PCR system (FIG. 9) and a sonic PCR system (FIG. 10). In each experiment, different concentrations of DNA were tested, ranging from 100 nanograms of DNA in the sample, down to 1 picogram of DNA in the sample. The experiment of FIG. 9 was performed using a commercially available thermal PCR machine, model AB7500, Applied Biosystems. This experiment shows the well-known characteristic of thermal PCR of showing increasing illumination, which demonstrates the log phase of DNA amplification, commencing at about cycle 23 for a more concentrated sample (e.g., 100 nanograms of DNA), but commencing at later cycles for less concentrated samples.

FIG. 10 shows that recognizable increases in DNA are measurable after only a few cycles when using sonic PCR. Even though it may be difficult to quantify from FIG. 10 how much DNA was originally present, something that is frequently done in the system of FIG. 9, FIG. 10 illustrates that one can effectively use sonic PCR to rapidly perform a qualitative determination whether a target DNA template is present. This is even more notably the case when one notes that each cycle of FIG. 9 was 120 seconds, whereas each cycle in FIG. 10 was only 13 seconds. Hence, FIG. 10 demonstrates the ability of sonic PCR to provide very rapid determinations of the qualitative existence of a target DNA template.

Experiments with various DNA/primer/polymerase systems have shown that adjustments may be required in order to improve the efficiency of sonic PCR with some systems. It is currently believed that various factors may play a role in lower efficiency in some systems. For example, the short cycle times that are possible using sonic PCR may not provide enough time for primers to migrate to the vicinity of polymerase activity until the numbers of DNA molecules increases significantly within the sample vial. Another possible source of inefficiency is using a temperature that is too low for a particular set of chemistry, such as the low temperature use of primers having a high melt temperature, or other temperature-sensitive factors. Yet another potential source of inefficiency is lowered activity of particular polymerases at temperatures significantly lower than the biological temperatures at which they operate in their normal environment. It is believed that increasing the temperature of sonic PCR operations can significantly improve the efficiency of the PCR in many circumstances. For example, increasing the temperature from room temperature to a biological temperature of a particular relatively low-temperature polymerase, or to a raised temperature, such as 60 degrees C. when using a conventional high-temperature PCR polymerase, is believed likely to improve the efficiency of sonic PCR in systems that do not show high activities at room temperature. For purposes of simplicity and speed, it is preferred that sonic PCR be performed at a substantially isothermal temperature, regardless what actual operating temperature is selected.

The present invention provides significant improvements over traditional thermocycler-based PCR systems. There is no need to utilize a polymerase enzyme that is thermostable at high temperatures, such as required for conventional thermal PCR. Rather, the temperature of sonic PCR can be adjusted for use with polymerase enzymes that would be unsuitable for use in conventional thermal PCR systems. Indeed, there is no need to operate at any particular temperature, particularly if a suitable control system is used to monitor the PCR process and increase or decrease the sonic energy as required or the duration of the dissociation stage, so as to account for differences in any particular amplification event, whether that be due to temperature, frequency, transducer, power, volume of sample, particular DNA being amplified, or other differences that may occur from one amplification to another, or if one only wishes to quantitatively determine the existence of a particular target DNA template. Because no temperature change is required between the various steps of sonic PCR, and because it is a simple matter to apply or discontinue the application of sonic energy quite rapidly, no wasted time need exist in changing from one step of sonic PCR to the next. The efficiency of sonic PCR results in exceedingly fast PCR cycles. The simplicity of a sonic PCR device allows it to be quite small and portable, and the low power required allows it to run on battery power. Even sophisticated sonic PCR devices, which may include a controller system and a fluorescence system, and may permit the sonic PCR to be performed at a range of substantially isothermic temperatures, can be quite small and portable. Using sonic PCR rather than the cumbersome traditional thermal PCR systems allows for amplifications and associated testing to occur in the field rather than the laboratory, thereby permitting extremely rapid identification of pathogens in connection with national security or agricultural operations or animal husbandry, potentially saving lives and a great deal of money. Many medical diagnostic tests may be accomplished in minutes in a point of care location.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for amplification of DNA, comprising the steps of:
    providing a reaction mixture cocktail including DNA to be amplified, a polymerase enzyme, nucleosides, and primers;
    providing a sonic energy source suitable for dissociating said DNA to be amplified from its double stranded form to single strands of complementary DNA;
    operating the sonic energy source in order to effect dissociation of double stranded DNA in the mixture into single strands of DNA without raising the temperature of said reaction mixture cocktail to a temperature which would effect thermal denaturation of the double stranded DNA;
    discontinuing operation of the sonic energy source in order to allow formation of double stranded DNA from the single strands of DNA without including a cooling step in order to allow formation of double stranded DNA;
    repeating operation of the sonic energy source and discontinuance of operation of the sonic energy source as many times as required to produce a desired amount of DNA.

2. The method of claim 1 further comprising the step of monitoring the status of amplification over time.

3. The method of claim 2 further comprising the step of operating the sonic energy source until the monitoring step indicates that dissociation is complete.

4. The method of claim 2 further comprising the step of discontinuing operation of the sonic energy source until the formation of double stranded DNA from single strands of DNA is complete.

5. The method of claim 1, wherein the step of operating the sonic energy source lasts two seconds, and the step of discontinuing operation of the sonic energy source lasts for 11 seconds.

6. The method of claim 1, wherein the sonic energy is at least 20 KHz.

7. The method of claim 1, wherein the sonic energy produced by the sonic energy source is at or near the resonance frequency of said sonic energy source.

8. The method of claim 1, further comprising the step of monitoring the observable presence of DNA amplification in order to provide a quantitative determination of the presence of a target DNA in a sample.

9. The method of claim 1, further comprising the step of raising the temperature of the sample above ambient temperature in order to improve efficiency of PCR.

10. A method for amplification of DNA, comprising the steps of:
    providing a reaction mixture cocktail including DNA to be amplified, a polymerase enzyme, nucleosides, and primers;
    providing a sonic energy source suitable for dissociating said DNA to be amplified from its double stranded form to single strands of complementary DNA;
    operating the sonic energy source in order to effect dissociation of double stranded DNA in the mixture into single strands of DNA;
    discontinuing operation of the sonic energy source in order to allow formation of double stranded DNA from the single strands of DNA;
    repeating operation of the sonic energy source and discontinuance of operation of the sonic energy source as many times as required to produce a desired amount of DNA,
    wherein said steps of operating the sonic energy source and discontinuing operation of the sonic energy source effect amplification of DNA without thermal cycling.

11. The method of claim 10 further comprising the step of monitoring the status of amplification over time.

12. The method of claim 11 further comprising the step of operating the sonic energy source until the monitoring step indicates that dissociation is complete.

13. The method of claim 12 further comprising the step of discontinuing operation of the sonic energy source until the formation of double stranded DNA from single strands of DNA is complete.

14. The method of claim 10, wherein the step of operating the sonic energy source lasts two seconds, and the step of discontinuing operation of the sonic energy source lasts for 11 seconds.

15. The method of claim 10, wherein the sonic energy is at least 20 KHz.

16. The method of claim 10, wherein the sonic energy produced by the sonic energy source is at or near the resonance frequency of said sonic energy source.

17. The method of claim 10, further comprising the step of monitoring the observable presence of DNA amplification in order to provide a quantitative determination of the presence of a target DNA in a sample.

18. The method of claim 10, further comprising the step of raising the temperature of the sample above ambient temperature in order to improve efficiency of PCR.

* * * * *